(12) United States Patent
Ueno et al.

(10) Patent No.: US 6,482,981 B2
(45) Date of Patent: Nov. 19, 2002

(54) METHOD FOR PRODUCING ACRYLIC ACID

(75) Inventors: Kouji Ueno, Himeji (JP); Masatoshi Ueoka, Himeji (JP); Sei Nakahara, Himeji (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/753,810

(22) Filed: Jan. 3, 2001

(65) Prior Publication Data
US 2001/0020111 A1 Sep. 6, 2001

(30) Foreign Application Priority Data
Jan. 14, 2000 (JP) ........................................ 2000-007057

(51) Int. Cl.⁷ .......................... C07C 51/42; C07C 51/16
(52) U.S. Cl. ........................ 562/600; 562/532; 562/608
(58) Field of Search ................. 562/600, 532, 562/608

(56) References Cited

U.S. PATENT DOCUMENTS

| | | | |
|---|---|---|---|
| RE32,241 E | 9/1986 | Saxer | 62/542 |
| 5,504,247 A | 4/1996 | Saxer et al. | 562/600 |
| 5,817,865 A | 10/1998 | Machhammer et al. | 560/208 |
| 6,252,110 B1 * | 6/2001 | Uemura | |

FOREIGN PATENT DOCUMENTS

| | | |
|---|---|---|
| EP | 0861820 | 2/1998 |
| EP | 0887334 | 12/1998 |
| JP | B 60-32615 | 7/1985 |

* cited by examiner

Primary Examiner—Sreeni Padmanadhan
Assistant Examiner—Farhad Forohar
(74) Attorney, Agent, or Firm—Mathews, Collins, Shepard & McKay, P.A.

(57) ABSTRACT

A method of producing highly purified acrylic acid in a high yield is provided. A method of producing acrylic acid including the steps of an oxidation step, an absorption step, a distillation step, a crystallization step, and a dimer decomposition step.

16 Claims, 1 Drawing Sheet

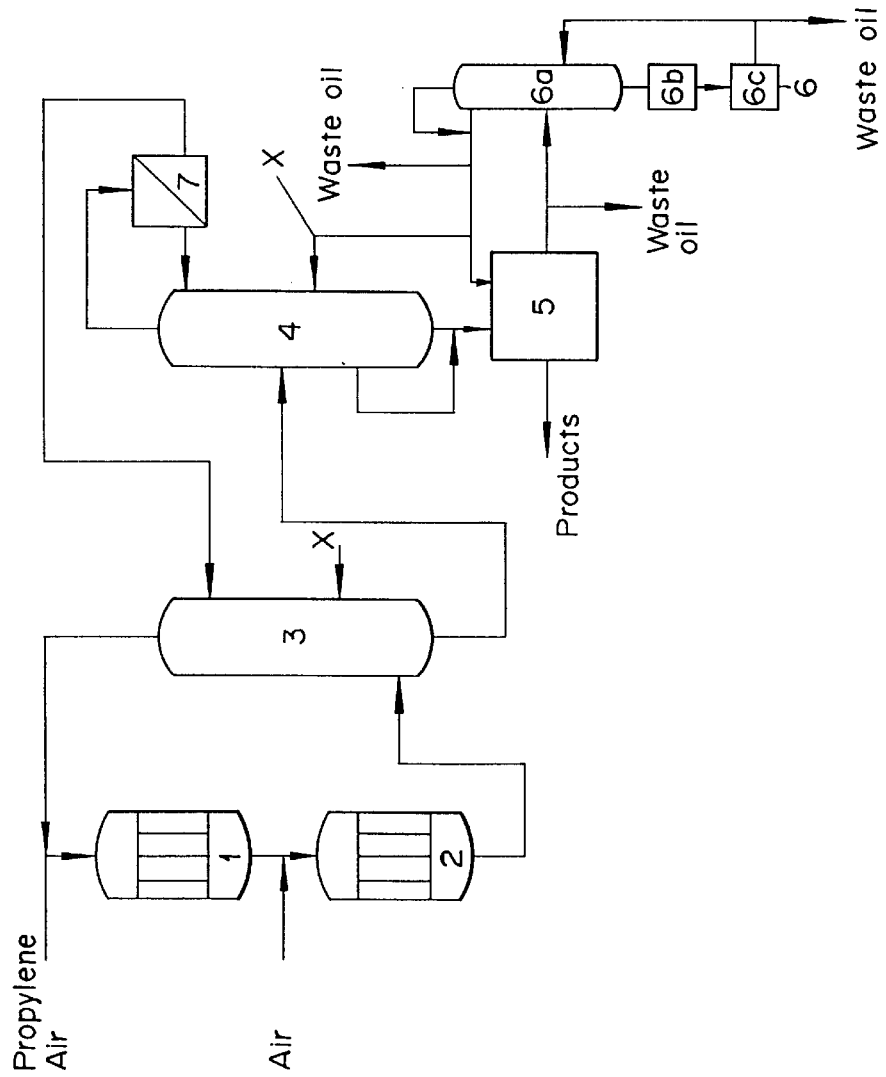
FIGURE

METHOD FOR PRODUCING ACRYLIC ACID

BACKGROUND OF THE INVENTION

1. Field of the Invention

The present invention relates to a method for producing acrylic acid. More particularly, it relates to a method for producing acrylic acid which adopts a crystallization process and an acrylic acid dimer decomposition process in the purifying step.

2. Description of the Related Art

Acrylic acid is used chiefly for producing acrylate that is an important raw material for textile fibers, surface coating materials, dispersants, and adhesives. In addition, recently, the use of acrylic acid for the raw material of highly water absorber has increased, and a highly purified acrylic acid having an impurity concentration of tens to hundreds of ppm by weight is required.

The propylene oxidizing method by which propylene and/or acrolein are oxidized in catalytic vapor phase oxidation is industrially common for the method of producing acrylic acid. When acrylic acid is produced by the propylene oxidizing method, in the oxidation process of propylene impurities such as water, acids such as propionic acid, acetic acid, and maleic acid, acetone, and aldehydes such as acrolein, furfural, and formaldehyde are by-produced. A gas containing these by-products is absorbed as an acrylic acid solution generally by contacting the gas with a solvent, and the resulting acrylic acid solution is purified by separating the solvent by the method of distillation, etc. and then additionally separating the light boiling point components and the high boiling point components.

In order to obtain a more highly purified acrylic acid from the thus obtained acrylic acid, trace impurities such as aldehydes which cannot be easily separated by distillation are separated by use of a treatment with chemical agents, and a distillation process following the treatment or crystallization process. However, in the above-mentioned method there are too many processes to produce the highly purified acrylic acid, and the apparatus and the operations therefor are also too complex. In addition, there is a drawback that the load of high temperature is put on the distillation of acrylic acid, and therefor the dimerization, and oligomerization, orpolymerization of acrylic acid occurs to decrease the yield of acrylic acid.

JP-A-9-227445 discloses a method of producing the highly purified acrylic acid by absorbing a gas containing the acrylic acid obtained by the catalytic gas phase oxidation with a high boiling point solvent, separating the absorbed mixture into a solvent and a crude acrylic acid by means of distillation, and then using a crystallization process. However, this method cannot also avoid reducing the yield of acrylic acid because of the occurrence of the dimerization of acrylic acid in the absorption process and the distillation process.

SUMMARY OF THE INVENTION

Therefore, an object of the present invention is to provide a method of producing the acrylic acid having a high purity in a high yield.

We have diligently studied the method of producing acrylic acid, and as a result have found that the above described object is attained by oxidizing propylene and/or acrolein by means of catalytic vapor phase oxidation, subsequently causing the obtained reaction mixture to be absorbed in a solvent, distilling the obtained product to obtain a crude acrylic acid from the column bottom portion and/or the column side portion, purifying the crude acrylic acid by use of a dynamic and static crystallization steps, feeding a residual mother liquid to a acrylic acid dimer decomposition step to collect acrylic acid, and returning the collected acrylic acid to at least one step selected from the group consisting of the crystallization step, the distillation step, and the absorption step.

That is, we have found that purifying the crude acrylic acid by use of the crystallization step can prevent the acrylic acid from further being dimerized, oligomerized, and polymerized, and can efficiently concentrate the dimer of acrylic acid, and subjecting the obtained concentrated dimer to the dimer decomposition step can easily collect the acrylic acid.

That is, the present invention relates to a method of producing acrylic acid, comprising the steps of oxidation, absorption, distillation purification, crystallization, and dimer decomposition, or the invention relates to a method for producing acrylic acid, comprising the steps of a) catalytic vapor phase oxidizing propylene and/or acrolein with a molecular oxygen containing gas;

b) introducing the obtained gaseous mixture to an acrylic acid absorption column, and contacting the mixture with a solvent to absorb the mixture as an acrylic acid solution;

c) subjecting the acrylic acid solution to distillation step to separate a crude acrylic acid substantially not containing solvent from the solution as a column bottom stream and/or a column side stream;

d) feeding the crude acrylic acid to a crystallization step to melt crystallize the acrylic acid and separate the acrylic acid into a purified acrylic acid and a residual mother liquid; and e) feeding the residual mother liquid to an acrylic acid dimer decomposition step to obtain a distillate, and feeding the distillate to at least one step selected from the group consisting of the crystallization step, the distillation step, and the absorption step.

The method of producing acrylic acid according to the present invention makes it possible to obtain the highly purified acrylic acid in a high yield.

The above and other objects, features and advantages of the present invention will become clear from the following description of the preferred embodiments.

BRIEF DESCRIPTION OF THE DRAWINGS

The accompanying drawing incorporated in and forming a part of the specification, illustrates several aspects of the present invention, and together with the description serve to explain the principles of the invention. In the drawing:

FIGURE is a block diagram showing a mode of the method of producing acrylic acid of the present invention.

DESCRIPTION OF THE PREFERRED EMBODIMENTS

The present invention will next be described following the steps.

Step a): Propylene and/or acrolein are catalytic vapor phase oxidized with a molecular oxygen containing gas.

Propylene and/or acrolein are oxidized in the presence of a known catalyst by contacting it with a molecular oxygen containing gas such as air and oxygen. The oxidation reaction is typically carried out by two stages. As the catalyst that used in the first stage of the oxidation, any catalyst can be used as long as the catalyst can be used for vapor phase oxidizing the raw material gas containing propylene to chiefly obtain acrolein. As the catalyst that used in the second stage of the oxidation, any catalyst can be used as long as the catalyst can be used for vapor phase oxidizing the raw material gas containing acrolein to chiefly obtain acrylic acid. For instance, examples of the catalyst used in the first stage include a complex oxide containing iron, molybdenum, and bismuth, and examples of the catalyst used in the second stage include catalysts containing vanadium as the essential component. The temperature of the oxidation reaction is typically a range of 200–400° C. (JP-A-64-63543, JP-A-63-93747, and JP-B-60-32615)

A gaseous mixture obtained in the catalytic gas phase oxidation reaction contains acrylic acid, a molecular oxygen containing gas, and the unreacted components in the reaction, and in addition as impurities contains water, acetic acid, propionic acid, maleic acid, acetone, acrolein, furfural, and formaldehyde and the like which are by-produced.

Step b): The gaseous mixture obtained in Step a) is introduced to an acrylic acid absorption column, and is contacted with a solvent to absorb the mixture as an acrylic acid solution.

The gaseous mixture is contacted with a solvent in order to collect acrylic acid from the gaseous mixture obtained in Step a). Though the solvent is not particularly limited as long as the solvent is possible to absorb acrylic acid and cause acrylic acid to be dissolved in the solvent, examples of the solvent include diphenyl ether, diphenyl, a mixture of diphenyl ether and diphenyl, water, and a water containing an organic acid produced from the process of purification of acrylic acid. Particularly water and/or a water containing an organic acid produced from the process of purification of acrylic acid are preferable. The obtained solution containing acrylic acid is referred to as acrylic acid solution (or aqueous acrylic acid solution).

As the method of contacting the gaseous mixture containing acrylic acid with the solvent, a known method of contact can be used. Examples of the method include a method of cross flow contact using a bubble-cap tray, uniflat tray, perforated tray, jet tray, bubble tray, and Venturi tray; and a method of counter current contact using a turbo grid tray, dual flow tray, ripple tray, kittel tray, structured packings such as gauze type packings, sheet type packings, and grid type packings, and random packings.

The gaseous mixture containing acrylic acid has a high temperature, but previously cooling the mixture or using a cooled solvent can prevent the solvent from scattering.

The obtained acrylic acid solution contains a small amount of the above-mentioned impurities besides the acrylic acid and solvent.

After Step b) was performed, the acrylic acid solution may be subjected to stripping step to remove the aldehydes contained therein as the impurity if necessary.

Step c): The acrylic acid solution is subjected to distillation step to separate a crude acrylic acid substantially not containing solvent therefrom as a column bottom stream and/or a column side stream.

The distillation column used in the present invention is not particularly limited as long as the column can separate the crude acrylic acid from the acrylic acid solution, however, a packed column and a tray column, etc. may be used.

Distilling the acrylic acid solution produces the acrylic acid solution that does not substantially contain solvent. This acrylic acid is referred to as acrude acrylic acid.

When water is used as an absorption solvent in Step b), typically in the known method, the aqueous acrylic acid solution contains 50–80% by weight of acrylic acid, 1–5% by weight of acetic acid, 10–40% by weight of water, and 0.5–5% by weight of the other impurities (acid such as maleic acid or propionic acid, and aldehyde such as furfural or formaldehyde etc).

An azeotropic solvent used in the method of obtaining the crude acrylic acid from the aqueous acrylic acid solution by use of azeotropic distillation has been variously described in patent publications or the like. One column distillation method by which water and acetic acid are simultaneously removed by use of one distillation column is described (refer to JP-B-46-18967, JP-B-46-20372, JP-B-46-22456, JP-B-46-34692, JP-B-49-21124, and JP-A-5-246941). Two column distillation method by which water is removed by use of an azeotropic distillation column, and acetic acid is removed by use of a low boiling point components separation distillation column is described (refer to JP-B-46-18966, JP-B-50-25451, JP-B-63-10691, JP-A-3-181440, JP-B-6-15495, and JP-B-6-15496).

When the purified acrylic acid is obtained by use of only the distillation method, the amount of acetic acid contained in the crude acrylic acid must be controlled to be about 1,000 ppm by weight or less. However, when the crystallization step is used in the present invention, the amount of acetic acid contained in the crude acrylic acid may be 2% by weight or less, preferably 1% by weight or less. The azeotropic solvent used at that time may be selected as appropriate.

Examples of the preferable azeotropic solvent include: a solvent containing at least one selected from the group consisting of heptane, dimethylcyclohexane, ethylcyclohexane, toluene, ethylbenzene, chlorobenzene, xylene, and a mixture of these compounds;

a solvent containing at least one selected from the group consisting of diethyl ketone, diisopropyl ketone, methyl propyl ketone, methyl isobutyl ketone, methyl t-butyl ketone, n- propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valerate, ethyl butyrate, dibutyl ether, and a mixture of these compounds and a solvent mixture of a solvent (A) containing at least one selected from the group consisting of heptane, dimethylcyclohexane, ethylcyclohexane, toluene, ethylbenzene, chlorobenzene, xylene, and a mixture of these compounds, and a solvent (B) containing at least one selected from the group consisting of diethyl ketone, diisopropyl ketone, methyl propyl ketone, methyl isobutyl ketone, methyl t-butyl ketone, n- propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valerate, ethyl butyrate, dibutyl ether, and a mixture of these compounds.

Examples of the more preferable solvent include a solvent containing at least one selected from the group consisting of heptane, toluene, ethylbenzene, xylene, and a mixture of these compounds; a solvent mixture of the above described solvent and a solvent containing at least one selected from the group consisting of ethyl acrylate, methyl methacrylate, ethyl methacrylate, and a mixture of these compounds; or a solvent containing at least one selected from the group consisting of ethyl methacrylate, diisopropyl ketone, n-propyl acrylate, n-butyl acetate, and a mixture of these compounds.

Performing azeotropic distillation by use of the above described solvent makes it possible to separate a crude acrylic acid from the aqueous acrylic acid solution, substantially not containing solvent and water, and containing 2% by weight or less acetic acid as a column bottom stream and/or a column side stream of the distillation column.

The azeotropic solvent is used slightly more than the amount required for causing water and acetic acid to azeotropically boil. (Refer to JP-A-9-157213, JP-A-10-237012, and JP-A-1-306052.)

The content of the acetic acid in the crude acrylic acid occasionally exceeds 2% by weight according to the content of the acetic acid in the aqueous acrylic acid solution. Even if the content of the acetic acid in the crude acrylic acid exceeds 2% by weight, the highly purified acrylic acid can be obtained in the following crystallization step. However, this case becomes economically disadvantageous because of the increase of the number of operations in the crystallization step. Accordingly, when the content of the acetic acid in the crude acrylic acid exceeds 2% by weight, preferably, the distillation which is the low boiling point components separation step is further performed to reduce the content of the acetic acid in the crude acrylic acid to 2% by weight or less. The low boiling point components separation therefor can be done by use of the known method of distillation or the like.

Step d): The crude acrylic acid is fed to a crystallization step to melt-crystallize it, and separate it into a purified acrylic acid and a residual mother liquid.

The crude acrylic acid obtained in Step c) is fed to the crystallization step. The crystallization step is performed dynamically and/or statically. The step is particularly preferably performed by a dynamic crystallization method or a combination of a dynamic crystallization method and a static crystallization method. In the static crystallization method, the substance to be processed moves only by free convection, and, on the other hand, in the dynamic crystallization method, the liquid to be processed moves by forced convection. The dynamic crystallization and static crystallization methods that are used therein are not particularly limited. (Refer to JP-B-53-41637, and JP-B-7-48311.)

Additionally, the number of needed crystallization stages depends on the purity of the acrylic acid which is necessary, and the number can be easily determined.

Dynamic crystallization and static crystallization each can be done in one or more stages. In this case, a multi processing method is advantageously carried out based on the principle of the counter current flow; at that time in each stage the substance crystallized is separated from the residual mother liquid after crystallization; and this crystallized substance is fed to each the following stage of further higher purity. On the other hand, the residue in crystallization is fed to each the following stage of further lower purity. Typically, the whole stage where the acid having higher purity than that of the fed raw acid is obtained is known as a purifying stage, and the whole other stage is known as a stripping stage. The stripping stage is performed to collect the acrylic acid in the mother liquid from the purifying stage. In the dynamic crystallization, when the purity of the acrylic acid became low, the crystallization becomes difficult. However, in the static crystallization, even if the purity of the acrylic acid became lower compared to the case of the dynamic crystallization, the crystallization is easy. Accordingly, the final mother liquid of the dynamic crystallization is further crystallized in the static crystallization in order to increase the recovering rate of acrylic acid.

Step e): The residual mother liquid obtained in Step d) is fed to an acrylic acid dimer decomposition step to obtain a distillate, and the obtained distillate is purified by use of any one of the above described crystallization step (d), the above distillation step (c) or the above absorption step (b); (d) and (c), (c) and (b) or (b) and (d); (d), (c) and (b).

The residual mother liquid obtained in Step d) is fed to the acrylic acid dimer decomposition step. In addition, a part of the crude acrylic acid obtained as the column bottom stream in the above mentioned distillation step (c) can be if necessary fed to the acrylic acid dimer decomposition step. The acrylic acid dimer decomposition step is not particularly limited as long as the step thermally decomposes the acrylic acid dimer to collect it as acrylic acid. For instance, the acrylic acid dimer decomposition step may be a step that decomposes the acrylic acid dimer and simultaneously distill the acrylic acid (refer to JP-B-61-35977 and JP-B-61-36501), more preferably the acrylic acid dimer decomposition step is a step using a tray column which is equipped with a thin film evaporator and a thermal decomposition vessel. (Refer to JP-A-11-12222.)

Regarding the acrylic acid dimer decomposition step, the case in which the acrylic acid dimer decomposition distillation column in which for instance the distillation column equipped with the thin film evaporator, and the thermal decomposition vessel are arranged in this order is used will be described. At least a part of the residual mother liquid, and if necessary a part of the crude acrylic acid obtained as the column bottom stream in the above described distillation step (c) are fed to the distillation column equipped with the thin film evaporator, and are distilled under conditions of for instance a pressure of 10–140 hPa and of a column bottom temperature of 60–120° C. The acrylic acid is distilled from the column top of this distillation column, and at least a part of the distilled acrylic acid is fed to at least one selected from the group consisting of the above mentioned crystallization step (d), the distillation step (c), and the absorption step (b). Advantageously, feeding the acrylic acid to the above mentioned crystallization step is economical. In addition, the bottom liquid from the above mentioned thin film evaporator is fed to the thermal decomposition vessel. In the thermal decomposition vessel, the acrylic acid dimer in the above mentioned bottom liquid is decomposed at a temperature within the range of 120–220° C., and then at least a part of the bottom liquid from the thermal decomposition vessel is circulated to the above mentioned distillation column.

In this method, compared with the conventional method of combining the distillation step and the acrylic acid dimer decomposition step, combining the crystallization step of the acrylic acid and the acrylic acid dimer decomposition step prevents not only the formation of the acrylic acid dimer to easily obtain the highly purified acrylic acid, but also can unexpectedly efficiently concentrate the acrylic acid dimer in the acrylic acid in the crystallization step, and the combination of the acrylic acid dimer decomposition step proved to be additionally effective for economically attaining a high yield.

The total amount of the residual mother liquid from the crystallization step may be fed to the acrylic acid dimer decomposition step, however, a part of the residual mother liquid can be also discharged outside from the system as a waste oil to avoid the concentration of the low boiling point impurities.

Moreover, when the total amount of the residual mother liquid from the crystallization step was fed to the acrylic acid dimer decomposition step, a part of the acrylic acid collected from the acrylic acid dimer decomposition step can be discharged outside from the system in order to avoid the concentration of the low boiling point impurities.

If necessary, before the residual mother liquid from the crystallization step is fed to the acrylic acid dimer decomposition step, the aldehydes and the maleic acid can be chemically pre-treated in order to make these compounds a high boiling point substance. The concentration of impurities in the acrylic acid to be collected from the dimer decomposition step is reduced. The processing agent used for the above-mentioned chemical pretreatment is not particularly limited as long as it reacts with aldehydes and maleic acid. However, examples of the agent include aliphatic amines, aromatic amines, hydrazine derivatives, and compounds having a mercapto group therein. (Refer to JP-B-48-31087, JP-A-49-30312, JP-B-58-37290, and JP-B-4-29658.)

FIGURE is a block diagram showing a mode of the method of producing acrylic acid of the present invention. In FIGURE propylene and air are fed to a first reactor 1. In this reactor 1 the catalytic gas phase oxidation reaction of converting propylene into acrolein is performed. To the obtained acrolein is additionally added air, and in the second reactor 2 the acrolein is oxidized to produce a gaseous mixture containing acrylic acid. The obtained gaseous mixture is introduced to an absorption column 3, and contacted with a solvent to absorb as an acrylic acid solution. The obtained acrylic acid solution is introduced to a distillation column 4, and distilled to separate it into the solvent and a crude acrylic acid that does not substantially the solvent. A distillate from the column top of distillation column 4 is separated into the solvent and an azeotropic solvent with an oil water separator 7. The separated azeotropic solvent is recycled to the distillation column 4, and on the other hand, the separated solvent is recycled to the absorption column 3. The crude acrylic acid that does not substantially contain the solvent is separated into a column bottom stream and/or a column side stream. The separated crude acrylic acid is fed to a crystallization unit 5. In the crystallization unit 5, the crude acrylic acid is separated into a purified acrylic acid and a residual mother liquid by combining a dynamic crystallization method and a static crystallization method. The purified acrylic acid is obtained as a product. On the other hand, because the residual mother liquid contains an acrylic acid dimer, the liquid is fed to an acrylic acid dimer decomposition step 6. A distillate containing the acrylic acid obtained by decomposing the dimer is fed, in order to collect the acrylic acid, to at least one selected from the group consisting of the absorption column 3 (in FIGURE, the distillate travels along x—x), distillation column 4, and crystallization unit 5. In FIG. 6a depicts a distillation column, 6b thin film evaporator, and 6c thermal decomposition vessel.

EXAMPLES

The present invention will next be described and illustrated by way of examples. However, the invention is not limited only to these examples.

EXAMPLE 1 (COMPARATIVE EXAMPLE)

For the catalysts for the first step and the second step, the catalysts having the following molar ratios respectively (except oxygen) of the catalyst composition (not containing the carrier composition) were prepared. (JP-B-60-32615)

The first step: $Co_4Fe_1Bi_1W_2Mo_{10}Si_{1.35}K_{0.08}$

The second step: $Mo_{12}V_{4.6}Cu_{2.2}Cr_{0.6}W_{2.4}$

The above mentioned catalyst for the first step (12.0 liters) was uniformly charged into a shell-and-tube reactor having ten steel tubes having an internal diameter of 25 mm, and a length of 3,000 mm, and then heated to 335° C. Separately, the above mentioned catalyst for the second step (12.0 liters) was uniformly charged into a shell-and-tube reactor having ten steel tubes having an internal diameter of 25 mm, and a length of 3,000 mm, and then heated to 260° C.

A gaseous mixture that is the raw material gas, containing propylene (8.0 vol. %), steam (6.1 vol. %), and oxygen (14.3 vol. %) was heated to 120° C. at a rate of 16.2 m³/hr (converted to NTP; hereinafter the volume of gaseous substance is converted to NTP.), and then fed to the first step reactor to perform the reaction.

The gaseous reaction effluent produced in the second step reactor was pre-cooled to 150° C. through use of a pre-cooler, and then fed to an acrylic acid absorption column made of stainless steel, equipped with bubble-cap-shelves having 20 plates, and has an internal diameter of 200 mm. To the absorption column was fed an aqueous solution containing hydroquinone (0.1 wt. %) at a rate of 1.7 kg/hr from the column top to absorb the effluent as an aqueous acrylic acid solution.

Then the aqueous acrylic acid solution was fed to the column top of a packed column that is made of stainless steel, and has an internal diameter of 100 mm and a packed length of 5 m, and into the packed column was bubbled air at a rate of 2.96 m³/hr from the column lower part while the column was being heated such that the temperature of the column bottom was 85° C., to strip acrolein or the like. An aqueous acrylic acid solution containing acrylic acid (70.9 wt. %), water (25.6 wt. %), acetic acid (2.0 wt. %), and the other components (acids such as maleic acid and propionic acid, and aldehydes such as furfurals and formaldehyde etc) (1.5 wt. %) was obtained at a rate of 5.20 kg/hr.

Subsequently, the obtained aqueous acrylic acid solution was distilled in an azeotropic distillation column. The azeotropic distillation column is equipped with dual flow trays having 60 plates and a distance of 147 mm between the plates, a distillation pipe at the column top portion, a raw material feeding pipe at the intermediate portion, and a column bottom solution withdrawing pipe at the column bottom portion.

An azeotropic separation was done under the conditions that toluene was used as the azeotropic solvent, the column top pressure was 173 hPa, the reflux ratio (the total mole number of the reflux per unit time/the total mole number of the distillate per unit time) was 1.35, and the amount (rate) of the raw material was 8.50 kg/hr.

A crude acrylic acid containing acrylic acid (96.9 wt. %), acetic acid (0.06 wt. %), water (0.03 wt. %), and acrylic acid dimer (2.0 wt. %) was obtained at a rate of 6.03 kg/hr from the column bottom.

Then, the crude acrylic acid was fed to the crystallization unit, and purified three times through use of the dynamic crystallization step. In addition, the residue after crystallization in the purifying stage was treated three times through the dynamic crystallization step and two times through the static crystallization step.

The dynamic crystallization was performed in a crystallization apparatus that had been described in JP-B-53-41637. That is, the apparatus is a metallic tube which has a length of 6 m, and an internal diameter of 70 mm, and which is equipped with a storage vessel in the lower portion. The apparatus can move the liquid stored in the storage vessel toward the higher portion of the tube by use of a circulation pump, and cause the liquid to flow along the internal wall of the tube as falling film. The surface portion of the tube is composed of a double jacket, and the jacket is controlled to have a constant temperature by use of a thermostat.

A series of operations in the dynamic crystallization were done according to the following procedures.

1. Crystallization: A crude acrylic acid is fed to the storage vessel, and caused to flow along the tubular wall surface as falling film by use of the circulation pump, to crystallize about 60–80 wt. % of the acrylic acid with the jacket temperature being reduced below the freezing point.

2. Sweating: The circulation pump is stopped, the jacket temperature is increased to the vicinity of the freezing point, and the acrylic acid is caused to sweat about 2–5 wt. % thereof. After sweating, the residual melt is pumped out.

3. Melting: The jacket temperature is increased beyond the freezing point, the crystal is caused to melt, and then it is pumped out.

In the above operations, the temperature and the level of solidification depend on each the step.

The static crystallization was performed in a crystallization apparatus that is a metallic tube that is equipped with a drawing-out cock in the lower portion, and has an internal diameter of 90 mm and a length of 1 m. The surface portion of the tube is composed of a double jacket, and the jacket is controlled to have a constant temperature by use of a thermostat.

A series of operations in the static crystallization were done according to the following procedures.

1. Crystallization: A crude acrylic acid is fed into the tube, and caused to freeze in an amount of about 60–80 wt. % with the jacket temperature being reduced below the freezing point.

2. Sweating: The residual melt after crystallization is withdrawn, and caused to sweat about 15–25 wt. % thereof with the jacket temperature being increased to the vicinity of the freezing point. After sweating, the sweat liquid is withdrawn.

3. Melting: The jacket temperature is increased beyond the freezing point to melt the crystal, and the melt is withdrawn.

A highly purified acrylic acid having a purity of 99.98 wt. % was obtained at a rate of 5.72 kg/hr. In addition, the residual mother liquid after crystallization which was concentrated through the stripping stage that was done five times contained acrylic acid (38.3 wt. %) and acrylic acid dimer (40.2 wt. %) as the main components, and was obtained at a rate of 0.31 kg/hr, but the liquid was abandoned.

The purification yield obtained from the azeotropic distillation step was only 94.9%.

EXAMPLE 2

The procedure of Example 2 was repeated except that 10% of the residual mother liquid from the crystallization step was abandoned, the remainder 90% thereof was fed to an acrylic acid dimer decomposition distillation column, and the acrylic acid collected from the column top was circulated to the stripping stage of crystallization step.

90% (0.28 kg/hr) of the residual mother liquid, similarly obtained as in Example 1 after the crystallization step, containing acrylic acid (38.3 wt. %) and acrylic acid dimer (40.2 wt. %) as the main components was fed to the middle portion of the acrylic acid dimer decomposition distillation column. The acrylic acid dimer decomposition distillation column has a structure of combination of a distillation column equipped with dual flow trays having 15 plates, a thin film evaporator, and a thermal decomposition vessel. The acrylic acid dimer decomposition distillation column was operated under the conditions that the thermal decomposition was done under the conditions that the internal temperature of the thermal decomposition vessel was 140° C., and the residence time within the vessel was 45 hrs; the thin film evaporator was controlled such that the column bottom temperature was 85° C.; the column top pressure was 33 hPa; and the reflux ratio was 0.9. The acrylic acid having an acrylic acid content of 85.2 wt. % was collected from the column top at a rate of 0.19 kg/hr. The collected acrylic acid was circulated to the crystallization unit. A highly purified acrylic acid having a purity of 99.94 wt. % was obtained at a rate of 5.88 kg/hr.

The purification yield from the azeotropic distillation step was 97.5%.

It is now confirmed whether the acrylic acid dimerization occurred when the collected acrylic acid was treated in the crystallization unit.

Since the amount rate of the collected acrylic acid was 0.19 kg/hr, and the acrylic acid content therein was 85.2 wt. %, the amount rate of pure acrylic acid was 0.16 kg/hr.

On the other hand, in Example 1, a highly purified acrylic acid having a purity of 99.98 wt. % was obtained at a rate of 5.72 kg/hr after the treatment in the crystallization unit; and a highly purified acrylic acid after the treatment (in the crystallization unit) of the acrylic acid collected from the acrylic acid dimer decomposition distillation column was obtained at a rate of 5.88 kg/hr; therefore the difference of 0.16 (5.88–5.72) kg/hr was brought by the collected acrylic acid.

Accordingly, it is confirmed that even if the acrylic acid collected from the acrylic acid dimer decomposition distillation column is treated in the crystallization unit, the dimerization, oligomerization, and polymerization of acrylic acid can be prevented.

EXAMPLE 3

The procedure of Example 3 was repeated except that the residual mother liquid from the crystallization step was not abandoned; all of the residual mother liquid was fed to the acrylic acid dimer decomposition distillation column; 90% of the acrylic acid collected from the column top was circulated to the stripping stage of the crystallization step; and 10% of them was abandoned.

All of the residual mother liquid similarly obtained as in Example 1, containing acrylic acid (38.3 wt. %) and acrylic acid dimer (40.2 wt. %) as the main components was fed to the middle portion of the acrylic acid dimer decomposition distillation column at a rate of 0.31 kg/hr.

The acrylic acid dimer decomposition distillation was done as in Example 2, and an acrylic acid having an acrylic acid content of 85.2 wt. % was collected from the column top at a rate of 0.21 kg/hr. 90% (0.19 kg/hr) of the collected acrylic acid was circulated to the crystallization unit. A highly purified acrylic acid having a purity of 99.94 wt. % was obtained at a rate of 5.88 kg/hr.

The purification yield obtained from the azeotropic distillation step was 97.5%.

EXAMPLE 4

An azeotropic distillation was done under the conditions that the aqueous acrylic acid solution obtained in Example 1 was used as the raw material; ethyl methacrylate was used as the azeotropic solvent; the column top pressure was 167 hPa; the reflux ratio was 0.41; and the amount rate of the raw material was 8.50 kg/hr. The distillation column described in Example 1 was used.

A crude acrylic acid containing acrylic acid (97.0 wt. %), acetic acid (0.3 wt. %), water (0.03 wt. %), and acrylic acid dimer (2.0 wt. %) was obtained at a rate of 6.04 kg/hr from the column bottom.

Then, the crude acrylic acid was subjected to the same crystallization step as in Example 1, and a residual mother liquid after the crystallization, containing acrylic acid (31.1 wt. %) and acrylic acid dimer (36.2 wt. %) as the main components was obtained at a rate of 0.38 kg/hr.

20% of the obtained residual mother liquid was abandoned, and the remainder 80% (0.30 kg/hr) was subjected to the same acrylic acid dimer decomposition step as in Example 2. An acrylic acid having an acrylic acid content of 70.5 wt. % was collected from the column top of the acrylic acid dimer decomposition distillation column at a rate of 0.22 kg/hr.

The collected acrylic acid was circulated to the crystallization unit. A highly purified acrylic acid having a purity of 99.95 wt. % was obtained at a rate of 5.88 kg/hr.

The purification yield obtained from the azeotropic distillation step was 97.4%.

EXAMPLE 5

An azeotropic distillation was done under the conditions that the aqueous acrylic acid solution obtained in Example 1 was used as the raw material; a solvent mixture of methyl methacrylate and toluene (the mixing ratio by weight: 35:65) was used as the azeotropic solvent; the column top pressure was 173 hPa; the reflux ratio was 1.30; and the amount of the raw material was 8.50 kg/hr. The distillation column described in Example 1 was used.

A crude acrylic acid containing acrylic acid (96.9 wt. %), acetic acid (0.03 wt. %), water (0.03 wt. %), and acrylic acid dimer (2.0 wt. %) was obtained at a rate of 6.02 kg/hr from the column bottom.

Then, the crude acrylic acid was subjected to the same crystallization step as in Example 1, and a residual mother liquid after the crystallization containing acrylic acid (32.8 wt. %) and acrylic acid dimer (38.4 wt. %) as the main components was obtained at a rate of 0.36 kg/hr. 10% of the obtained residual mother liquid was abandoned, and the remainder 90% (0.33 kg/hr) was subjected to the same acrylic acid dimer decomposition step as in Example 2. An acrylic acid having an acrylic acid content of 78.6 wt. % was collected from the column top of the acrylic acid dimer decomposition distillation column at a rate of 0.21 kg/hr.

The collected acrylic acid was circulated to the crystallization unit. A highly purified acrylic acid having a purity of 99.97 wt. % was obtained at a rate of 5.87 kg/hr.

The purification yield obtained from the azeotropic distillation step was 97.6%.

The entire disclosure of Japanese Patent Application No. 2000-7057 filed on Jan. 14, 2000 including specification, claims, drawing and summary are incorporated herein by reference in its entirety.

What is claimed is:

1. A method for producing acrylic acid, the method comprises the steps of:
   a) catalytic vapor phase oxidizing propylene and/or acrolein with a molecular oxygen containing gas;
   b) introducing the obtained gaseous mixture to an acrylic acid absorption column, and contacting the mixture with a solvent to absorb the mixture as a solution containing acrylic acid;
   c) subjecting the solution containing acrylic acid to a distillation step to separate a crude acrylic acid substantially not containing solvent from the solution as a column bottom stream and/or a column side stream;
   d) feeding the crude acrylic acid to a crystallization step to melt crystallize the acrylic acid and separate the acrylic acid into a purified acrylic acid and a residual mother liquid;
   e) feeding the residual mother liquid to an acrylic acid dimer decomposition step to obtain a distillate; and
   f) feeding at least a part of the distillate to the crystallization step (d).

2. A method according to claim 1, wherein the contact in the step b) is performed in the presence of at least one member selected form the group consisting of a bubble-cap tray, uniflat tray, perforated tray, jet tray, bubble tray, and Venturi tray, a turbo grid tray, dual flow tray, ripple tray, kittel tray, gauze packings, sheet packings, grid packings and randam packings.

3. A method according to claim 2, wherein the contact in the step b) is performed in the presence of the bubble-cap tray.

4. A method according to claim 1, wherein the contact in the step b) is a counter current contact.

5. A method according to claim 1, wherein the distillation in the step c) is performed with at least one member selected from the group consisting of a packed column and a tray column.

6. A method according to claim 1, wherein the distillation in the step c) is performed by use of at least one member selected from the group consisting of one column distillation method and two column distillation method.

7. A method according to claim 1, wherein the solvent which absorbs the acrylic acid is water, and the distillation step is an azeotropic distillation step, or an azeotropic distillation step and a low boiling point components separation step following the azeotropic distillation step.

8. A method according to claim 7 further comprising in the azeotropic distillating step using at least one solvent selected from the group consisting of heptane, dimethylcyclohexane, ethylcyclohexane, toluene, ethylbenzene, chlorobenzene, xylene, and a mixture of these compounds as an azeotropic solvent.

9. A method according to claim 7 further comprising in the azeotropic distillation step using at least one azeotropic solvent selected from the group of diethyl ketone, diisopropyl ketone, methyl propyl ketone, methyl isobutyl ketone, methyl t-butyl ketone, n- propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valerate, ethyl butyrate, dibutyl ether, and a mixture of these compounds.

10. A method according to claim 7 further comprising in the azeotropic distillation step, using at least one azeotropic solvent selected from the group consisting of heptane, dimethylcyclohexane, ethylcyclohexane, toluene, ethylbenzene, chlorobenzene, and xylene, and at least one azeotropic solvent selected from the group consisting of diethyl ketone, diisopropyl ketone, methyl propyl ketone, methyl isobutyl ketone, methyl t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valerate, ethyl butyrate, and dibutyl ether.

11. A method according to claim 1, wherein the crystallization in the step d) is performed by use of a dynamic crystallization method and/or a static crystallization method.

12. A method according to claim 1, wherein the acrylic acid dimer decomposition is performed with a distillation column equipped with a thin film evaporator and a thermal decomposition vessel.

13. A method according to claim 12, wherein a pressure of the distillation column is in the range of 10 to 140 hPa.

14. A method according to claim 12, wherein a column bottom temperature of the distillation column is in the range of 60 to 120° C.

15. A method according to claim 12, wherein a temperature of the decomposition vessel is in the range of 120 to 220° C.

16. A method according to claim 1, wherein in the step e) the distillate is fed to the crystallization step.

* * * * *